(12) United States Patent
Ohmori et al.

(10) Patent No.: US 9,931,034 B2
(45) Date of Patent: Apr. 3, 2018

(54) OPTICAL COHERENCE TOMOGRAPHY

(71) Applicant: Tomey Corporation, Nagoya-shi (JP)

(72) Inventors: Tsutomu Ohmori, Nagoya (JP); Masahiro Yamanari, Nagoya (JP); Satoshi Sugiyama, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 15/427,289

(22) Filed: Feb. 8, 2017

(65) Prior Publication Data
US 2017/0231493 A1   Aug. 17, 2017

(30) Foreign Application Priority Data

Feb. 12, 2016   (JP) ................................. 2016-024422

(51) Int. Cl.
*A61B 3/14* (2006.01)
*A61B 3/15* (2006.01)
(Continued)

(52) U.S. Cl.
CPC ............ *A61B 3/154* (2013.01); *A61B 3/0025* (2013.01); *A61B 3/0075* (2013.01); *A61B 3/102* (2013.01);
(Continued)

(58) Field of Classification Search
CPC ......... G02B 1/11; A61B 3/154; A61B 3/0025; A61B 3/0075; A61B 3/1005; A61B 3/1225
(Continued)

(56) References Cited

U.S. PATENT DOCUMENTS

| 7,468,997 | B2 | 12/2008 | Jayaraman |
| 2006/0279741 | A1 | 12/2006 | Hirata et al. |

(Continued)

FOREIGN PATENT DOCUMENTS

| JP | 2005-156540 A | 6/2005 |
| JP | 2006-337239 A | 12/2006 |

(Continued)

OTHER PUBLICATIONS

Al-Hafeez Dhalla et al., "Complex conjugate resolved heterodyne swept source optical coherence tomography using coherence revival", Biomedical Optics Express, vol. 3, No. 3, p. 633-649, (2012).

(Continued)

*Primary Examiner* — Jack Dinh
(74) *Attorney, Agent, or Firm* — Shumaker, Loop & Kendrick, LLP

(57) ABSTRACT

An optical coherence tomography includes a light source, a light separator, a light generator configured to generate interference light, a detector configured to detect the interference light, a first optical element, and at least one of second optical elements comprising a pair of surfaces, and performs forming a tomographic image of a subject. The first optical element is arranged on a measurement light path so as to be closest to the subject, and satisfies at least one of following conditional formulas:

| $-(W-S)<U-2Z<X-W;$ | [a2] |
| $U-2Z<-W;$ and | [b1] |
| $U-2Z>X-W+S,$ | [c2] |

W: a predetermined operation distance
U: a depth of interest
S: a range of interest (Continued)

X: a distance which is greater than W+U+S and minimal among distance(s) between the pair of surfaces Z: a shallowest position of the area of interest relative to an origin position.

19 Claims, 10 Drawing Sheets

(51) Int. Cl.
    *A61B 3/00*     (2006.01)
    *A61B 3/10*     (2006.01)
    *A61B 3/12*     (2006.01)
    *G02B 1/11*     (2015.01)
    *G01B 9/02*     (2006.01)

(52) U.S. Cl.
    CPC .......... *A61B 3/1005* (2013.01); *A61B 3/1225* (2013.01); *G01B 9/02004* (2013.01); *G01B 9/02078* (2013.01); *G01B 9/02091* (2013.01); *G02B 1/11* (2013.01)

(58) Field of Classification Search
    USPC ........................................................ 351/208
    See application file for complete search history.

(56) References Cited

U.S. PATENT DOCUMENTS

| | | |
|---|---|---|
| 2008/0024788 A1 | 1/2008 | Shimizu et al. |
| 2008/0031410 A1 | 2/2008 | Shimizu et al. |
| 2008/0252901 A1 | 10/2008 | Shimizu et al. |
| 2008/0316495 A1 | 12/2008 | Hirata et al. |
| 2009/0079991 A1 | 3/2009 | Hirata et al. |
| 2009/0244547 A1 | 10/2009 | Ozawa |
| 2009/0273790 A1 | 11/2009 | Shimizu et al. |
| 2011/0181889 A1 | 7/2011 | Kabetani et al. |
| 2015/0077757 A1 | 3/2015 | Tanaka et al. |

FOREIGN PATENT DOCUMENTS

| | | |
|---|---|---|
| JP | 2007-510143 A | 4/2007 |
| JP | 2007-526620 A | 9/2007 |
| JP | 2007-278868 A | 10/2007 |
| JP | 2011-527418 A | 10/2011 |
| JP | 2014-081301 A | 5/2014 |
| JP | 2014-522105 A | 8/2014 |
| JP | 2015-102537 A | 6/2015 |
| JP | 2015-523578 A | 8/2015 |
| WO | 2005/001401 A2 | 1/2005 |
| WO | 2005/047813 A1 | 5/2005 |
| WO | 2010/003684 A1 | 1/2010 |
| WO | 2013/016249 A2 | 1/2013 |
| WO | 2014/018950 A1 | 1/2014 |

OTHER PUBLICATIONS

Sekhar, S.C. et al., "Theoretical Analysis of Complex-Conjugate-Ambiguity Suppression In Frequency-Domain Optical-Coherence Tomography", Biomedical Imaging: From Nano To Macro, 2008. ISBI 2008. 5th IEEE International Symposium On IEEE, Piscataway, NC, USA, May 14, 2008, p. 396-399.

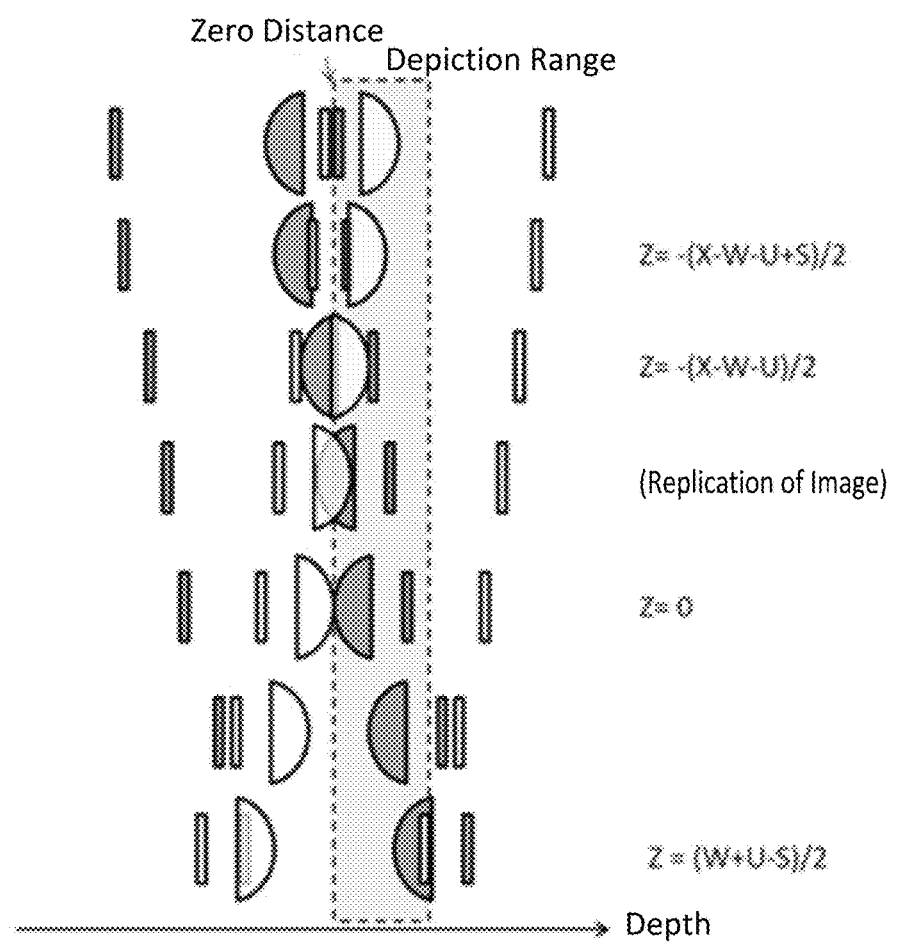

OPTICAL COHERENCE TOMOGRAPHY

TECHNICAL FIELD AND BACKGROUND

The present disclosure relates to a preferred device configuration used in a wavelength sweeping type optical coherence tomography.

An optical coherence tomography (hereinbelow referred to as "OCT") is for measuring a tomographic image of a living subject by using interference of light, and is commonly used especially in ophthalmology as a method of obtaining two-dimensional or three-dimensional tomographic images of a cornea and a retina. In recent years, a Fourier domain method has been employed. The Fourier domain method includes a spectral domain OCT (hereinbelow referred to as SD-OCT) where a tomographic image is obtained by detecting spectral information using a spectroscope, and a swept source OCT (hereinbelow referred to as SS-OCT) where a tomographic image is obtained by detecting a spectral interference signal using a wavelength sweeping light source. The SS-OCT is also termed optical frequency domain imaging (OFDI), and is a technique the same as the OFDI (for example, see Japanese Patent Application Publication No. 2007-510143).

In the Fourier domain method, light is introduced to an interferometer from a light source of which wavelength has a broad band, and the light is outputted to a subject such as an eyeball. Scattered light is reflected from the subject, and the scattered light is detected by the interferometer. A raw signal detected (interference signal) is an interference spectrum, and a distribution of scattered light intensity scattered in a depth direction of the subject is obtained by performing Fourier analysis on the interference signal. Further, a two-dimensional distribution of scattered light intensity or a three-dimensional distribution of scattered light intensity can be obtained by scanning a beam irradiated to the subject in a lateral direction, and this distribution of scattered light intensity corresponds to a tomographic image of the subject. This is termed OCT tomographic image or the like.

In the SD-OCT, the interference spectrum is obtained by using light of which wavelength has a broad band as a light source and an array sensor via an interferometer for detection. In the SS-OCT, since wavelength sweeping light of which wavelength is swept with high speed is used, the detection of the interference spectrum is obtained as a time-domain function.

However, in both of the methods, due to the nature of Fourier transform, a mirrored image of the OCT tomographic image appears symmetrically relative to a zero frequency corresponding to a zero point and relative to a Nyquist frequency being a depth where a detection range terminates. The mirrored image relative to the latter frequency can be easily eliminated by a filter, however, the mirrored image relative to the zero frequency is difficult to be eliminated and is disincentive as an artifact in the measurement. Hereinbelow, only the mirrored image relative to the zero frequency will be considered.

In both of the OCT methods of the Fourier domain method, the broader the wavelength band to be used is, the higher resolution capability becomes.

However, in the SD-OCT, a low-coherent light source is used in principle, due to an increase in a wavelength band width. Therefore, with the high resolution capability, sensitivity for the interference signal largely reduces as a depth of the image increases. To solve this problem, wavelength resolution capability of the detector needs to be enhanced, however, this is difficult in terms of a configuration of the detector. On the other hand, in the SS-OCT, since the wavelength is swept timewise and coherence of the light source is determined by a substantially instantaneous line width, the directly opposing influence of the sensitivity reduction relative to the high resolution and the depth is not big.

As the SS-OCT, an attempt using an SSG-DBR (Super Structure Grating Distributed Bragg Reflector) laser of a communication band (for example, see Japanese Patent Application Publication No. 2005-156540), and a method using a multimode wavelength sweeping light source with an external cavity including a polygon scanner (for example, see Japanese Patent Application Publication No. 2007-510143 and Japanese Patent Application Publication No. 2007-526620) have been suggested. Especially, the latter has been used as a practical ophthalmic OCT. Further, in recent years, a technique which is sped up by using a MEMS (microelectromechanical system) has been suggested, and not only the multimode wavelength sweeping light source but also a single-mode wavelength sweeping light source such as a DBR laser and a VCSEL (vertical cavity surface emitting laser) delivers practical performance (for example, see U.S. Pat. No. 7,468,997, Japanese Patent Application Publication No. 2006-337239, Japanese Patent Application Publication No. 2007-278868, Japanese Patent Application Publication No. 2014-522105, Japanese Patent Application Publication No. 2015-102537, and Japanese Patent Application Publication No. 2015-523578).

A characteristic substantially largely different between the multimode wavelength sweeping light source and the single-mode wavelength sweeping light source lies in the instantaneous line width. The latter usually oscillates light with a narrower line width. The line width is strongly associated with the coherence. Specifically, using a coherence length for evaluation of coherence, a coherence length of the multimode wavelength sweeping light source is approximately 20 mm at longest, whereas a coherence length of the single-mode wavelength sweeping light source can be equal to or greater than 100 mm By making a condition of optical interference signal measurement appropriate, the tomographic image can be obtained in a depth range corresponding to the coherence length. In reality, since reflection and the scattered light of the subject are detected, the depth range in which the tomographic image can be obtained with an effective sensitivity is approximately a half of the coherence length.

For example, since even the multimode wavelength sweeping light source has a sufficient coherence in an anterior eye and a posterior eye, it has been applied as an ophthalmologic instrument. Further, the single-mode wavelength sweeping light source expands a possibility of an OCT or an eye axial length measurement device which can target all kinds of eyes (16 mm to 40 mm).

SUMMARY

Technical Problem

As described above, in the SS-OCT, a long coherence length is advantageous to obtain the tomographic image of a deep position with high sensitivity. This means that since the sensitivity is not compromised even at the deep position, and locations where the tomographic image with high sensitivity can be obtained are not limited to a vicinity of a point where a distance to the subject from the light source and a distance of a reference light path becomes equal (hereinbelow referred to as zero point).

However, the reflection and the scattered light of the subject are not the only ones that appear as the optical interference signal in the actual measurement. Reflection of an optical element such as a lens contributes to the signal, and the optical interference signal related to a lens arrangement appears as the artifact at a part of the OCT tomographic image. Especially in a case where a coherence length is extremely long as in the single-mode wavelength sweeping light source, the artifact appears even in the depth range which did not need to be considered before. Specifically, the depth range up to a depth corresponding to a coherence length related to a depiction range needs to be considered.

A surface of the optical element, especially of a lens that is used significantly close to an area of interest, that transmits light therethrough and a surface of the subject causes reflections to occur. In the tomographic image, signals of these reflections occur at positions clearly shallower than the area of interest.

Since measurement light is not assumed to effectively reach to rearward of the area of interest of the subject in most cases, the artifacts of the reflections are not assumed to occur in the rearward of the area of interest.

However, in a case where a multiple reflection (number of times of the reflection is an odd number equal to or greater than three) is detected, its reflection signal appears at a position which is apart by a distance equal to a total of light paths along which the light had traveled from the light source. Therefore, apparently, a tomographic image is generated for each multiple reflection at a position which is apart from the surface of the subject by the total distance the multiple reflection had traveled from the light source, and a plurality of such tomographic images generated by the multiple reflections appear repeatedly at intervals at such positions. Since an amount of light decreases due to reflection in reality, only the multiple reflections of the surface of the subject and the surface of the optical element of which reflectances are relatively large remain practically and become the artifacts. Accordingly, depending on the light path along which the light travels, signals of the multiple reflections can appear at positions deeper than the area of interest of the subject.

Although the artifact can somewhat be reduced by dispersing the reflection signals of the surfaces of the lens and the subject by optical design, it takes much effort to disperse all of reflections of many optical elements in the long depth range while collecting the measurement light to the subject, and thus it is difficult to take the multiple reflections into consideration completely.

Regarding reflection of an optical element, usually, a reflectance of BK7 which is a typical glass is approximately 4% (−14 dB) for example. Further, reflection of incident light to the subject cannot be ignored, and its reflectance at a cornea is approximately 2.5% (−16 dB). Reflected light occurs with a large reflectance, not only at an obviously transparent body such as the cornea, but also at a skin surface, for example. Since a reflectance of the scattered light from a fundus is said to be approximately −50 to −80 dB of that of the incident light for example, it is assumed that not only the single reflection of the optical element but also the multiple reflection blend in the OCT tomographic image as the artifacts.

Further, since the SS-OCT is the Fourier domain method, the mirrored image of the OCT tomographic image which appears symmetrically with the OCT tomographic image relative to the zero point also needs to be considered for its blending issues as the artifact, which makes the problem complicated. Especially in a case where the light path length can be changed, a positional relationship between the signal of the subject and the mirrored image artifact changes, and thus a range within a light path length adjustment range, where the mirrored image artifact overlaps the signal of the subject, needs to be eliminated.

Japanese Patent Application Publication No. 2014-081301 discloses an effective method for the problem that the reflection signal of the optical element blends in as the artifact due to the coherence length, for example. However, Japanese Patent Application Publication No. 2014-081301 is limited to the single reflection, and does not mention the multiple reflection.

In the multimode wavelength sweeping light source of which coherence length is relatively short, the range in which the OCT tomographic image is detected is optically limited up to a depth approximately equal to the coherence length, and thus it is thought that the above-mentioned problem caused by the multiple reflections does not occur.

However, in the multimode wavelength sweeping light source as well, there is a known problem that can be considered in a similar framework to the above-mentioned interference signals of the multiple reflections of the optical element. In the multimode wavelength sweeping light source provided with the external cavity, light oscillated by being multiple-reflected in the cavity of the light source is outputted repeatedly. As A-H. Dhalla at el, "Complex conjugate resolved heterodyne swept source optical coherence tomography using coherence revival", BIOMEDICAL OPTICS EXPRESS Vol. 3, No. 3 633-649 discloses "(section 2.2) This concept can be extended to place any integer number of virtual cavities in the sample arm", although the range in which the OCT tomographic image is detected is limited to the depth approximately equal to the coherence length for example, the OCT tomographic images appear repeatedly at intervals in a state including the artifacts at positions which are apart by distances in which a depth corresponding to a length of the cavity of the multimode wavelength sweeping light source is added to (or subtracted from) total distances of the light path along which the light travels from the light source. If a size of the external cavity competes with the subject, the artifact can blend in a desired tomographic image.

What should especially be taken into consideration are the artifacts of the surfaces of the subject and the optical element due to the single reflection which appear at the positions shallower than the area of interest, and the artifact of the three-times reflection at the surface of the subject and/or the surface of the optical element which can appear at the position deeper than the area of interest and blend in the tomographic image.

For the multiple reflection, the light is reflected at the surface of the optical element closest to the surface of the subject and apart by a predetermined operation distance W from the surface of the subject, is reflected at the surface of the subject in a region shallower by a depth U from the area of interest, and then is reflected at the surface of the optical element again. When this occurs, the reflection of the surface of the optical element appears at a position which is apart by the operation distance W from the surface of the subject to the rearward side. If the operation distance W is greater than a size of the subject, the reflection of the surface of the subject appears behind the subject.

Further, if a pair of surfaces of at least one optical elements, other than the surface of the optical element closest to the subject, that causes two reflections of the three-times reflections, is present in a measurement light path or a reference light path, the reflections of the surface of the subject and of the surfaces of the other optical elements appear at positions which are apart rearwardly by a distance X, which is a distance between the surfaces of the at least one optical elements in the pair. Especially, if the distance X is greater than a sum of the operation distance W and the size of the subject, the artifact of the optical element closest to the subject appears behind the subject.

Further, generally, even when the coherence length is relatively short, the light amplified by being multiple-reflected in the light source is superimposed in the multimode wavelength sweeping light source as described above. Due to this, the artifact can appear at the position deeper than the area of interest. Even this case can be discussed similarly to the above-described case of the multiple reflections with the pair of the surfaces of the at least one optical elements with the distance X therebetween.

As above, in the measurement of the tomographic image of the deep position by the SS-OCT, an appropriate optical arrangement and the distance from the optical element to the subject need to be considered thoroughly such that the artifacts are avoided. However, there has been no proposal of a device configuration based on the surface of the optical element and the surface of the subject arranged to have the predetermined operation distance therebetween, and the relationship with the pair of the at least one optical elements in the measurement light path and the reference light path, especially assuming the single reflection and the multiple reflection.

Solution to Technical Problem

An optical coherence tomography disclosed herein comprises: a light source configured to change a wavelength of light to be outputted; a light separator configured to separate outputted light outputted from the light source into measurement light irradiated to a subject and reference light; a light generator configured to generate interference light by multiplexing reflected light from the subject and the reference light; a detector configured to detect the interference light; a processor; a memory storing computer-readable instructions therein, the computer-readable instructions, when executed by the processor, causing the optical coherence tomography to perform: forming a tomographic image of the subject based on a result by the detector; a first optical element arranged on a measurement light path so as to be closest to the subject and intersect substantially perpendicularly with an optical axis of the measurement light path, the measurement light path being a light path of the measurement light and the reflected light from the subject; and at least one of second optical elements comprising a pair of surfaces, the pair of surfaces of the at least one of the second optical elements being present in at least one of the light source, the measurement light path, and a reference light path being a light path of the reference light, the pair of surfaces of the at least one of the second optical elements intersecting substantially perpendicularly with an optical axis of the outputted light, the measurement light, or the reference light, wherein the first optical element satisfies at least one of following conditional formulas:

$-(W-S) < U-2Z < X-W;$ [a2]

$U-2Z < -W;$ and [b1]

$U-2Z > X-W+S,$ [c2]

W: a predetermined operation distance being a distance between a subject-side surface of the first optical element and a surface of the subject U: a depth of interest being a depth from the surface of the subject to an area of interest of the subject S: a range of interest being a depth range of the area of interest X: a distance which is greater than W+U+S and minimal among distance(s) between the pair of surfaces of at least one of second optical elements Z: a shallowest position of the area of interest relative to an origin position where a difference between a length of the measurement light path and a length of the reference light path becomes zero.

Advantageous Effects

The above conditional formulas are found relative to the position Z of which origin is a shallowest position of the area of interest where the artifacts (including the mirrored image) of the single reflection and the three-times reflection of the surface of the subject and the surface of the optical element do not overlap the desired tomographic image of the area of interest having the range S, with respect to the predetermined operation distance W and the depth U to the area of interest or the distance X between the pair of surfaces of the at least one optical elements, if the pair is present.

By the above condition being satisfied over an entirety of the adjustment range of a light path length adjustment unit, a possibility that the artifacts overlap the tomographic image of the area of interest can be eliminated. The conditions are similarly considered even if the light path length adjustment is not an issue of concern for an operator, thus the possibility that the artifacts overlap the tomographic image of the area of interest can be eliminated.

In the OCT with such conditions, the operator can obtain the tomographic image of the area of interest without worrying about the artifacts blending therein. Due to this, an advantageous usefulness can be achieved in that ophthalmologic misdiagnoses are reduced, especially in a diagnosis of a biological sample, particularly in an ophthalmologic OCT and an eye axial length measurement device.

BRIEF DESCRIPTION OF DRAWINGS

FIG. 5B is a diagram schematically showing B-scan tomographic images measured when the light path adjustment is performed in the optical coherence tomography of the third embodiment, virtually including the area outside of the depiction range;

DETAILED DESCRIPTION

Figure 1:
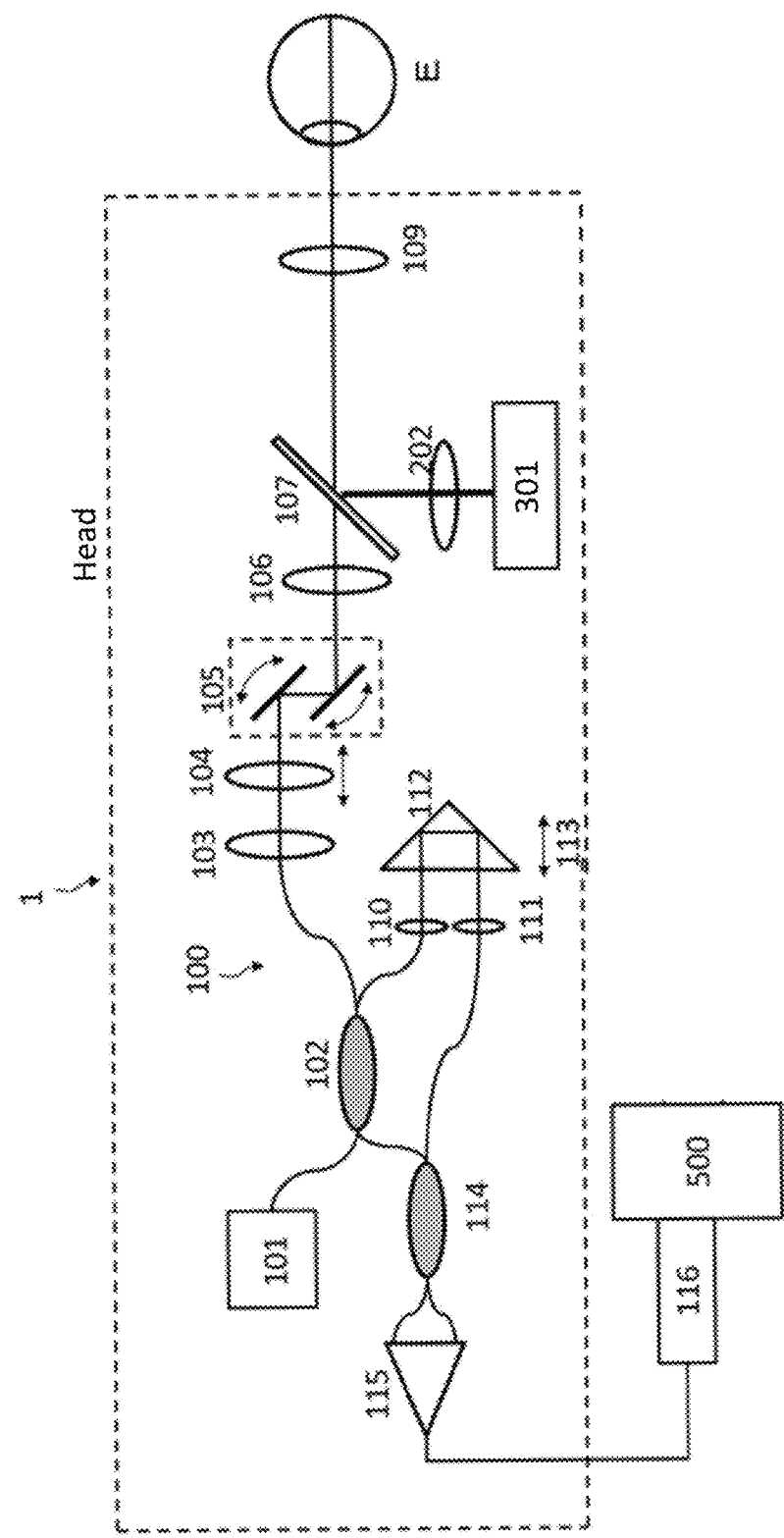
FIG. 1 shows a configuration of an optical system of an optical coherence tomography of a first embodiment according to the present application.

Referring to the drawings, an optical coherence tomography of a first embodiment according to the disclosure herein will be described below.

First Embodiment

FIG. 1 is a diagram showing a major configuration of an optical coherence tomography 1 of a first embodiment according to the disclosure herein. It should be noted that, although a subject herein is a human eye (eyeball) and a tomographic image to be obtained includes a retina at a fundus in the present embodiment, the present disclosure is not limited thereto, and a vitreum at a shallower position, or a chorioid and a sclera at a deeper position may be included.

The optical coherence tomography 1 comprises an interference optical system 100 for obtaining the tomographic image of the fundus of a subjected eye E non-invasively by using a technique of interference light.

A configuration of the interference optical system 100 will be described below. The interference optical system 100 is constituted of components from a wavelength sweeping light source 101 (hereinafter also referred to as OCT light source) to an ADC (AD converter) 116 configured to convert interference light from analog to digital.

Light outputted from the light source 101 passes through a fiber, and is split by a fiber coupler 102 into measurement light to be inputted to a collimator lens 103 and reference light to be inputted to a collimator lens 110. The measurement light inputted to the collimator lens 103 passes through a focus lens 104, a Galvano mirror 105, a lens 106, a dichroic mirror 107, and an objective lens 109, and is irradiated to the fundus of the subjected eye E. Then, the measurement light reflected from the fundus of the subjected eye E passes through, in a reversed route, the objective lens 109, the dichroic mirror 107, the lens 106, the Galvano mirror 105, the focus lens 104, the collimator lens 103, and the fiber coupler 102, and is inputted to one input portion of a fiber coupler 114. It should be noted that the fiber coupler 102 is an example of "light separator" in the claims.

Although not clearly shown in the drawing, there may be two or more measurement lights. There may be a case where the measurement light is split in a fiber light path and a plurality of the collimator lenses 103 is provided, or a case where the measurement light is split after having been outputted from the collimator lens 103. This splitting may be performed according to wavelength bands.

The dichroic mirror 107 is set to allow light of which wavelength is, for example, equal to or greater than 900 nm (the light from the OCT light source 101) pass therethrough but to reflect light of which wavelength is shorter than 900 nm including visible light, and can be connected to another optical system. For example, FIG. 1 shows a case where the dichroic mirror 107 is connected to a vision-fixation target 301 to make measurement easy by encouraging a vision-fixation of an examinee. Further, an anterior eye camera optical system for leading a beam to a pupil center such that a predetermined operation distance is obtained by optical design by appropriately positioning a head, and a fundus image obtaining unit such as a SLO (scanning laser ophthalmoscope) and a fundus camera for obtaining a planar image of the fundus may be provided, and unlike the measurement light, these may be appropriately set according to a wavelength of a light source to be used.

The reference light split by the fiber coupler 102 and inputted to the collimator lens 110 is reflected at a prism 112, passes through a collimator lens 111, and is inputted to another input portion of the fiber coupler 114.

Here, the prism 112 is moved along an optical axis and controlled to be able to change and adjust a reference light path length by a controller 113. For example, the prism 112 can move for a distance L along the optical axis. In the present embodiment, the reference light path length can be adjusted within a range of L to 2L by moving the prism 112. Normally, the prism 112 is moved by the controller 113 such that the reference light path length and a measurement light path length become equal before OCT shooting, and is fixed during measurement.

The measurement light and the reference light inputted to the fiber coupler 114 are multiplexed in the fiber coupler 114, inputted to a balance detector 115 as interference lights, and converted to an electric signal (interference signal). It should be noted that the two interference lights outputted from the fiber coupler 114 have phases different by 180 degrees from each other, and by these two interference lights being inputted to the balance detector 115 and differential-amplified, common noise is cancelled and only interference light to be the interference signal is amplified. Here, in a case where an influence of noise content such as the common noise is low, a simple one-input detector may be employed. In the case where there are two or more measurement lights, plural detectors may be employed. It should be noted that the coupler 114 is an example of "light generator" in the claims.

The interference signal outputted from the balance detector 115 is sampled as a digital signal in the ADC 116 and inputted to a calculator 500 constituted of a CPU, a memory, and the like, while A-scan data which is a tomographic signal in a depth direction is obtained by the sampled interference signal being Fourier-transformed, and the A-scan data is stored in the memory of the calculator 500.

At that occasion, a timing of the sampling may be at regular frequency intervals (regular wavenumbers) based on a k-clock signal sent by a k trigger generator (not shown) provided in a light source portion or out of the light source portion. Since a wavelength sweep of the wavelength sweeping light source 101 does not always vary at a constant frequency relative to a sweep time, this is a method of correcting the sampling effectively. Therefore, instead of using the k-clock signal, a process of scaling data sampled at certain times may be performed on a function indicating frequency for a predetermined sweep time, or on a sweep profile obtained simultaneously.

The Galvano mirror 105 scans horizontally (in an x-axial direction) and vertically (in a y-axial direction) relative to the subjected eye E, and in this case, a control signal is inputted from the calculator 500. By scanning the Galvano mirror 105 in the x-axial and y-axial directions, two-dimensional tomographic images or a three-dimensional tomographic image of the fundus of the subjected eye E can be obtained.

Figure 2A:
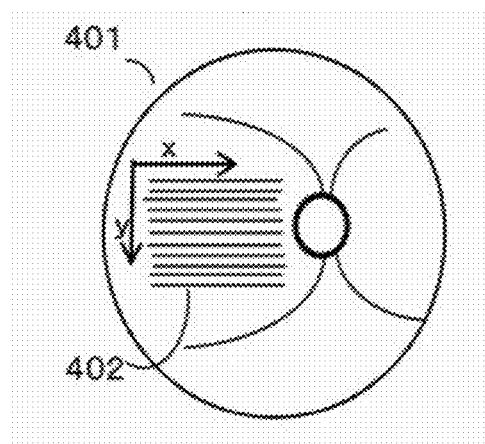
FIG. 2A is a diagram showing a concept of obtaining a tomographic image by the optical coherence tomography of the first embodiment.
Figure 2B:
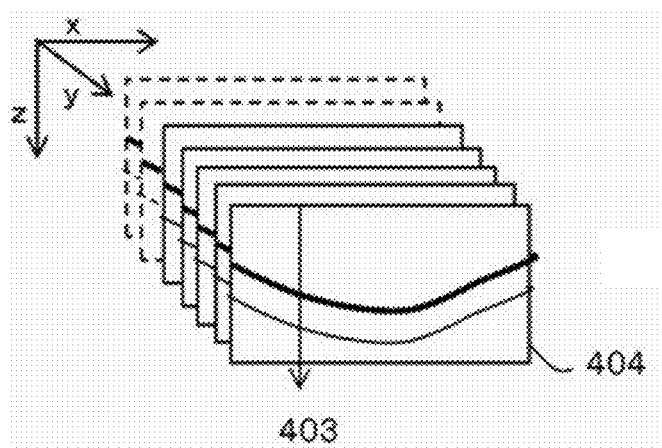
FIG. 2B is a diagram showing a concept of obtaining the tomographic image by the optical coherence tomography of the first embodiment.
Figure 2C:
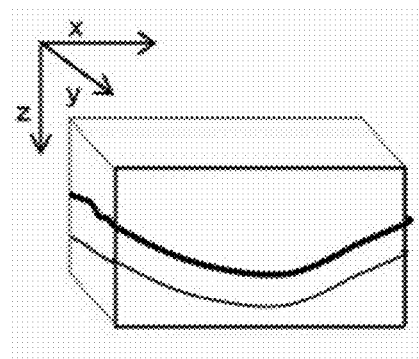
FIG. 2C is a diagram showing a concept of obtaining the tomographic image by the optical coherence tomography of the first embodiment.
Figure 2D:
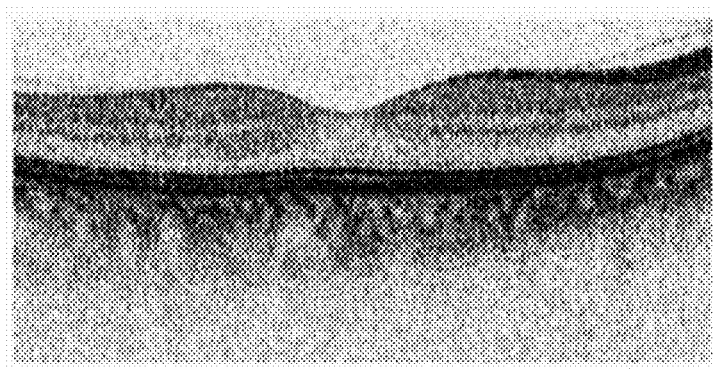
FIG. 2D is a diagram showing an example of an actual measurement of obtaining the tomographic image by the optical coherence tomography of the first embodiment.
Figure 2E:
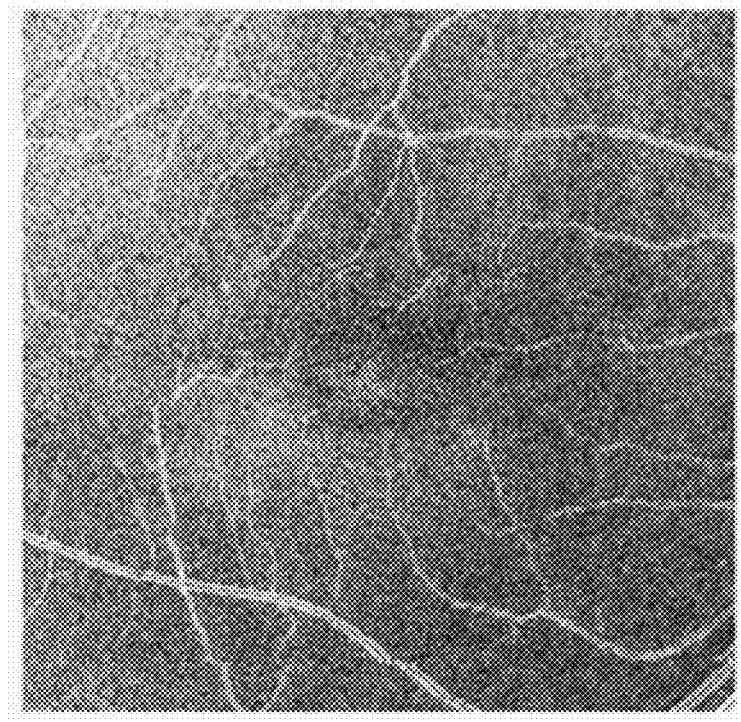
FIG. 2E is a diagram showing an example of an actual measurement of obtaining the tomographic image by the optical coherence tomography of the first embodiment.

FIGS. 2A to 2E show how the tomographic images (B-scan images) are obtained by the interference optical system 100. FIG. 2A shows an example of scan of the measurement light at a fundus retina 401 of the subjected eye E, and FIG. 2B shows an example of a plurality of the two-dimensional tomographic images (B-scan images) of the fundus retina 401 obtained by the scan of the measurement light. Further, FIG. 2C shows an example of a three-dimensional tomographic image of the fundus generated in the present embodiment. It should be noted that an x axis indicates a B-scan direction and a y axis indicates a C-scan direction in FIGS. 2A to 2C. Further, a z axis in FIGS. 2B and 2C indicates a depth direction of an A-scan signal, that is, a depth direction of the fundus. Each of FIGS. 2D and 2E shows an OCT image which is actually shot and displayed on a monitor. FIG. 2D shows one of the B-scan images corresponding to FIG. 2B, and FIG. 2E shows, after the three-dimensional tomographic image corresponding to FIG. 2C is obtained, a front image representing the three-dimensional tomographic image in an XY plane obtained by summing scattered light intensity in the z direction. The front image is known as an en face image.

Here, in the present embodiment, the predetermined operation distance W=44 mm, a depth U to the retina being an area of interest=20 to 36 mm, a range of interest S=4 mm assuming the retina, are adopted. All of these are optical distances.

In optical design, the operation distance W may vary so as to have a predetermined value according to a predetermined condition, however, it often has a constant value. Therefore, it is preferable that an interface is provided which can detect whether an optical element that is the closest to the subject (the objective lens 109 in the present embodiment) is positioned relative to the subject with a predetermined distance therebetween or not, or whether the position of the optimal element is misaligned forward or rearward. Further, it is more preferable to be provided with a configuration that optimizes the position of the optical element such that the optical element is automatically positioned at the position which is apart by the predetermined distance from the subject.

The depth U has the range to measure retinas corresponding to different axial lengths of human eyes, and hereinbelow, a case where the axial length corresponds to an actual range of 18 to 30 mm will be described. This range covers a majority of human eyes. In the conditional formulas in the claims, all values of the depth U are included.

What causes multiple reflections which can blend in the tomographic image is an optical element intersecting substantially perpendicularly with the optical axis. As far as FIG. 1 shows, each of the collimator lens 103, the focus lens 104, the lens 106, and the objective lens 109 in the measurement light path is the optical element. Further, each of the collimator lenses 110 and 111, and the prism 112 in the reference light path is also the optical element. In the present embodiment, all of the lenses except for the objective lens 109 are apart by 200 mm or greater from the subjected eye E. Further, since each of distances between the respective lenses is equal to or greater than 80 mm, artifacts of these lenses and the like do not appear closer to the tomographic image than an artifact of reflection of the objective lens 109 (within the operation distance of 44 mm between the objective lens 109 and the subject), and thus the artifacts are not considered here. Further, a discussion can be simplified on a premise that reflection signals adjacent to each other approximately by a thickness of a lens appear at a substantially same position.

Figure 3A:
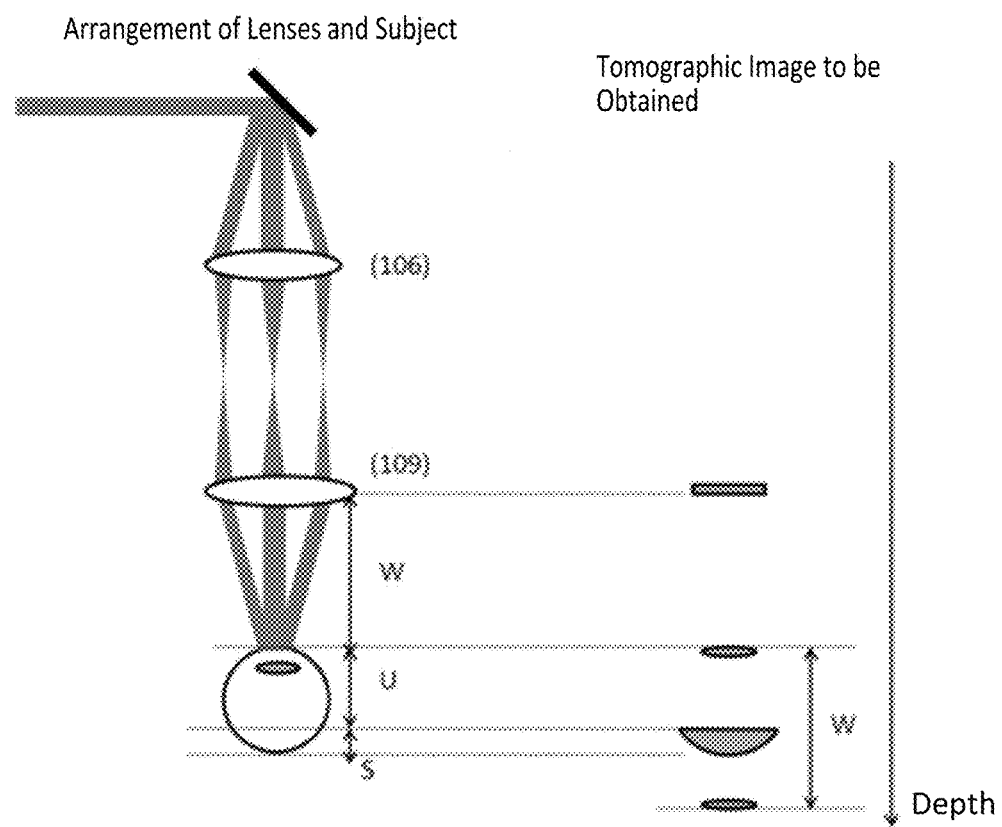
FIG. 3A is a diagram schematically showing B-scan tomographic images measured when a light path adjustment is performed in the optical coherence tomography of the first embodiment, virtually including an area outside of a depiction range.

The tomographic image occurs on the above condition is shown schematically as in FIG. 3. FIG. 3A shows a profile of the tomographic image logically obtained from the interference signal. A reflection signal of a subject-side surface of the objective lens 109 appears at a position shallower by the operation distance W from a surface of the subject. Further, a reflection signal reflected at the surface of the subject appears at a position shallower by the depth U from the area of interest. Further, a reflection signal which is reflected three times on the surface of the subject, on the objective lens 109, and on the surface of the subject in this order appears at a position deeper by the operation distance W from the surface of the subject.

Between the objective lens 109 and the surface of the subject, not only the three-times reflection but also 5-times or more reflection is assumed. To ignore these multiple reflections, it is preferable to provide an appropriate reflectance reduction such as an antireflection coating. Since a retinal signal has intensity that is approximately −50 to −80 dB of intensity of the measurement light, it is preferable that the antireflection coating that makes a reflectance especially equal to or less than 1% is given relative to OCT measurement light in order to neutralize an effect of the 5-times or more multiple reflections. In the present embodiment, a wavelength of 980 to 1100 nm is used as OCT measurement light for the retina, and thus the antireflection coating is given especially for that wavelength range. Other than that, a wavelength of 810 to 870 nm is used as the OCT measurement light for retina, generally.

It should be noted that, other than the antireflection coating, the artifacts can be relatively reduced by broadening the reflection signal by performing dispersion compensation which is optimal to the subject based on a fact that a dispersion of a light path of the subject and a dispersion of a light path of the reflection signal are different. As a method of the dispersion compensation, a dispersion compensation processing may be performed to a signal from the balance detector 115 by using software upon when the tomographic image is formed in the calculator 500, or the dispersion compensation may be performed by using hardware such as an optical component.

Figure 3B:
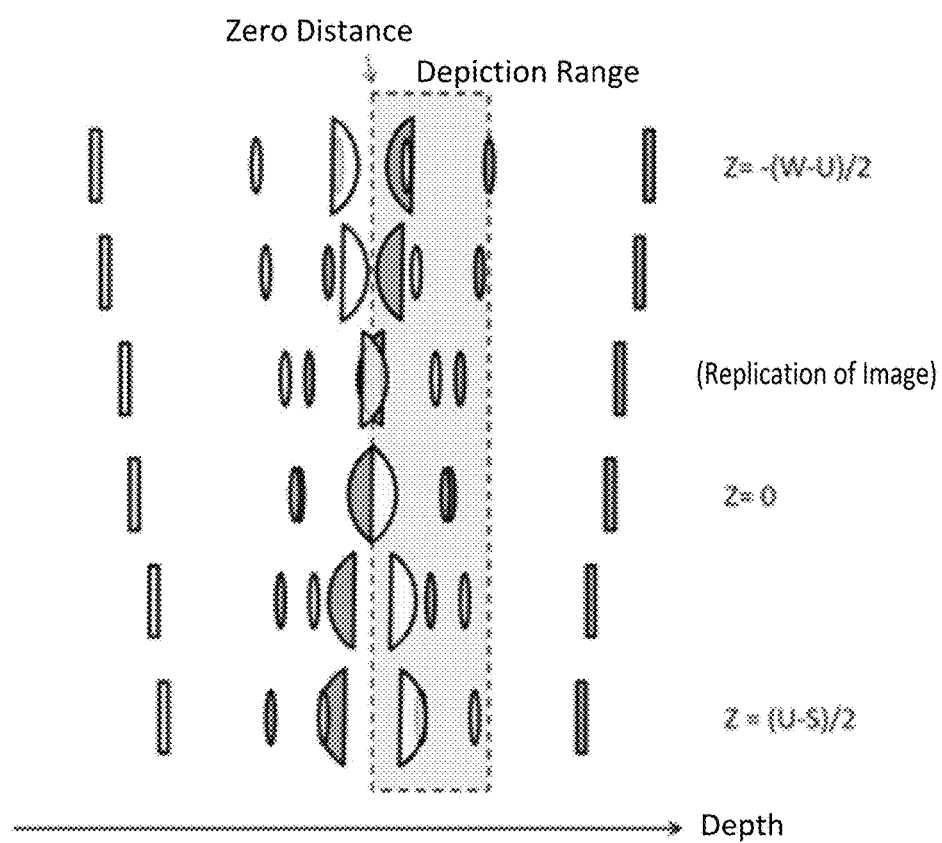
FIG. 3B is a diagram schematically showing B-scan tomographic images measured when the light path adjustment is performed in the optical coherence tomography of the first embodiment, virtually including the area outside of the depiction range.

Here, FIG. 3B shows the tomographic images relative to various values of a position Z that an operator can obtain as a depiction range when a continuous light path length adjustment is performed, by virtually including a situation outside of the depiction range as well. Here, mirrored images of the tomographic images which are symmetrical relative to a zero distance characterized in Fourier domain OCT are also displayed. The mirrored images are distinguishable from the tomographic images for convenience in the drawing, however, they cannot be distinguished from each other in reality.

In FIG. 3B, the light path length adjustment is performed with Z=0, and the area of interest moves to a deep position in the depiction range as the position Z becomes deep. In conjunction with that, the mirrored images of the reflection signal of the surface of the subject and the reflection signal of the objective lens move to shallow positions. In this case, until the position Z moves to (U−S)/2=8 mm, the reflection signal of the objective lens does not reach the area of interest regardless of a value of the depth U, and thus a depth of the position Z can be freely determined within a range of Z=0 to 8 mm On the other hand, when the position Z becomes shallower by the light path length adjustment, the mirrored image of the area of interest moves to the deep position, and the reflection signal does not reach the area of interest regardless of a value of the depth U, until the position Z moves to −(W−U)/2=−4 mm. However, since the mirrored image appears overlapping the tomographic image in the range of Z=0 to −4 mm, the tomographic image looks replicated. This range is a known problem as a range where the tomographic image of the area of interest cannot be correctly obtained, and thus a discussion thereof is omitted here. In some cases, such tomographic image may be allowable.

As described above, a range where the artifacts do not overlap the tomographic image is the range of Z=−4 to 8 mm, and substantially the depth position can be freely determined in the range of Z=0 to 8 mm.

Although it is especially effective in a case where a coherence length is short or in a case where a band of a detector is small, the measurement is often performed in a state where the value of the position Z is close to 0 with which a theoretically highest sensitivity can be expected. When such measurement is performed under the condition of the present embodiment, since a range of the depth U is 16 mm, a light path length adjustment range needs to be 32 mm. Even in this case, the artifacts do not overlap the tomographic image under the condition of the present embodiment.

However, since the depth position can be freely determined substantially in the range of Z=0 to 8 mm relative to any value of the depth U, as long as the range of the depth U is equal to or greater than 12 mm considering a case where Z=8 mm and S=4 mm, there is no problem if a light path length adjustment amount is shorter than 16 mm In this case, a coherence length that allows the tomographic image of 12 mm or greater to be detected, namely a coherence length of 24 mm or greater, is required.

The above explanation has been made considering that the depth U and the position Z can vary depending on subjected eyes. This complex relationship will be organized below.

The depth U, the position Z, and the light path length adjustment are associated deeply with one another. In a case where the depiction range is limited, when the light path length adjustment is performed always according to the depth U with the value of the position Z unchangeable as described above, the depth U and twice of the light path length adjustment amount are in a correspondence relationship. On the other hand, considering the overlap of the tomographic image with the mirrored image due to these images moving in opposite directions in the light path length adjustment, a travel amount of the position Z coincides with the light path length adjustment amount. By a range of U−2Z showing an overlap position of the artifacts as above, the light path length adjustment range expressed as the range of the depth U and the range of the position Z can deal with the complexity created by independent changes in the depth U and the position Z in a same frame.

Actually, when Z<(U−S)/2 and Z>−(W−U)/2 which are calculated based on the positional relationship of the artifacts considered as above are associated with each other, a formula [a1] S<U−2Z<W is obtained.

For example, in the case where the light path length adjustment amount is 16 mm at maximum as described above, U−2Z is in a range of 4 to 44 mm with the range of Z=0 to 8 mm, even if the light path length is changed relative to any value of the depth U. The U−2Z satisfies the above conditional formula.

Notably, in this case, the depiction range needs to have a length which is equal to or greater than a total value of the maximum value (U−S)/2 of the position Z with a value of the range S added thereto, and the coherence length is estimated twice the length, preferably equal to or greater than U+S. More generally, the coherence length is preferably equal to or greater than W−U+S and equal to or greater than U+S, considering an amount which is an absolute value (W−U)/2 of the position Z on its negative region with the value of the range S added thereto.

Figure 3C:
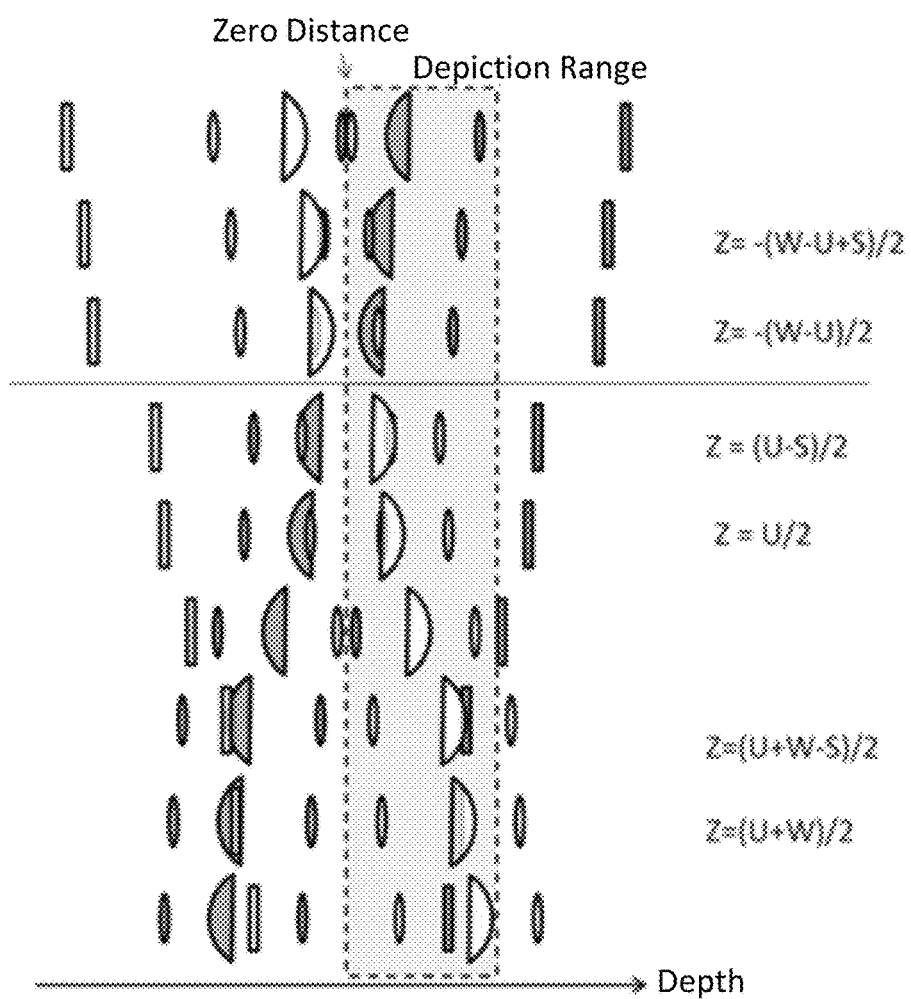
FIG. 3C is a diagram schematically showing B-scan tomographic images measured when the light path adjustment is performed in the optical coherence tomography of the first embodiment, virtually including the area outside of the depiction range.

An example has been described as above in which the artifacts do not overlap the area of interest in a certain range. However, even when the range shown in FIG. 3B is further expanded, all variables in the range where the artifacts do not overlap the area of interest are formulated in association with U−2Z, and the following three formulas are derived. The outline is shown in FIG. 3C. The depth U and the light path length adjustment amount may be determined so as to fall within such range.

$$U-2Z<-W \qquad [b1]$$

$$W+S<U-2Z \qquad [c1]$$

$$-(W-S)<U-2Z<0 \qquad [d1]$$

Since the absolute value of the position Z in the present embodiment is 14 mm or greater in the range of the position Z in these three inequalities, the depiction range needs to be equal to or greater than the value. Therefore, in each of the above inequalities, a condition of long coherence length is given. This is clearly included in the above-mentioned condition of coherence length.

The present embodiment has been described considering the continuous light path length adjustment. However, since the conditional formulas are discrete formulas, there would be no problem if the light path length adjustment range partially has discontinuous values.

Further, if the light path length adjustment is not considered to be an issue, the position Z can change according to the depth U which is a parameter of the subject. Especially, U−Z is invariable relative to the predetermined operation distance W, and U−2Z takes a range equaling only the change amount of the depth U. Even in this case, if the conditional formulas fall within the range, it is possible to avoid the artifact of the reflection of the lens overlapping relative to the surface of the subject and the operation distance W.

Second Embodiment

An OCT according to a second embodiment of the present disclosure will be described. Here, only points different from the first embodiment will be described and explanation of common points will be omitted.

In the measurement of optical coherence tomographic image of the retina, observation of a state of a fundus surface is an important element to identify a measurement point, and thus a fundus image obtaining unit is often provided. As the fundus image obtaining unit, a fundus camera and an SLO are used. Especially, in order to realize the fundus camera and the SLO capable of performing a real-time measurement, it is preferable to use infrared light of which wavelength is equal to or greater than 750 nm to avoid making the subject feel uncomfortable. Further, it is required to use a wavelength different from that of the OCT measurement light.

Figure 4:
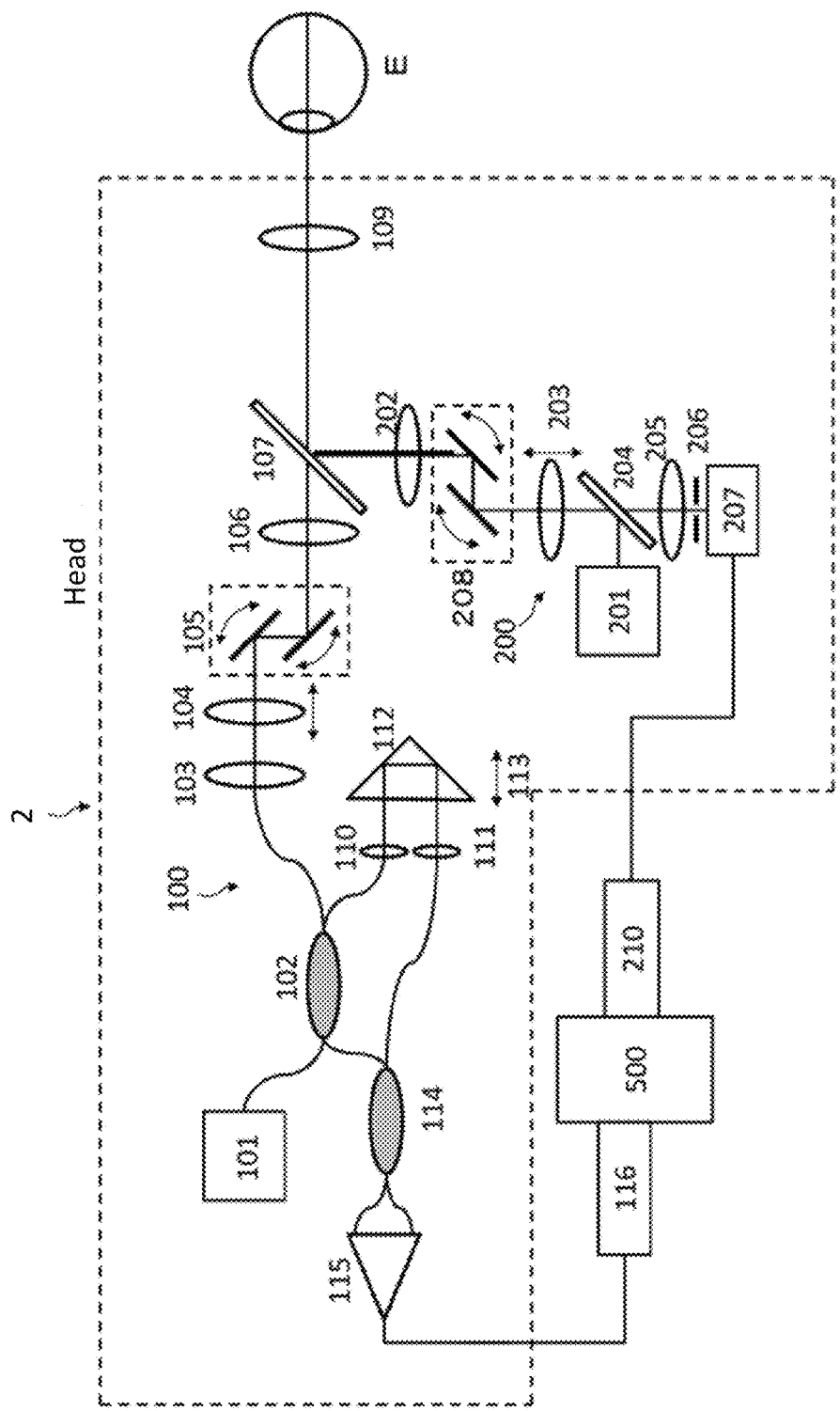
FIG. 4 is a diagram shows a configuration of an optical system of an optical coherence tomography of a second embodiment according to the present application.

FIG. 4 shows an example of an OCT provided with the SLO. Although a configuration of the OCT optical system is almost same as the configuration shown in FIG. 1, in FIG. 4, the vision-fixation target is not shown and replaced by the SLO.

(SLO Optical System 200)

An SLO optical system 200 is constituted of components from an SLO light source 201 to an ADC 210. The SLO light source 201 is configured to obtain an image of the fundus non-invasively by using a laser diode. It should be noted that, in the present embodiment, a laser diode of which wavelength is 850 nm is employed as the SLO light source 201. The SLO light source 201 is not limited to the laser diode of the present embodiment, and it may be another light source, for example, an LED (light-emitting diode).

Measurement light outputted from the SLO light source 201 (hereinbelow, referred to as SLO measurement light in order to distinguish it from another light) is reflected at a mirror 204. Here, light irradiated to the fundus and reflected light from the fundus travel along a same path. Therefore, in order to separate the irradiation light and the reflected light, a half mirror, a beam splitter or the like which reflects and transmits light in a predetermined ratio is employed as the mirror 204. A polarization beam splitter may also be employed as the mirror 204 to reduce unintentional scattering light and noise light caused by reflection within the optical system.

Thus, a part of the SLO measurement light is reflected at the mirror 204, inputted to a focus lens 203, passes through a scanning device 208 and a lens 202, and then is inputted to the dichroic mirror 107. The inputted SLO measurement light is reflected at the dichroic mirror 107, passes through the objective lens 109, and is irradiated to the fundus of the subjected eye E. The focus lens 203 is controlled to move on the optical axis such that the SLO measurement light irradiated to the fundus focuses on the fundus.

The SLO measurement light reflected at the fundus passes through, in the reversed route, the objective lens 109, the dichroic mirror 107, the lens 202, the scanning device 208, and the focus lens 203, and is inputted to the mirror 204. A part of the SLO measurement light inputted to the mirror 204 transmits the mirror 204, is inputted to a lens 205 and collected therein, passes through a pinhole 206, is received by a light detector 207, converted to an electrical signal, and then is inputted to an ADC 210.

Here, the scanning device 208 is configured to scan the SLO measurement light relative to the fundus of the subjected eye in the x-axial and the y-axial directions similarly to the Galvano mirror 105 in the above-mentioned optical system 100, and the data of the front image of the fundus can be obtained by scanning an irradiation position of the SLO measurement light by the scanning device 208. The scanning device 208 is not limited to the Galvano mirror, and may be a resonant scanner or a polygon mirror, or may have a combined configuration of the Galvano mirror and the polygon mirror. A two-dimensional MEMS mirror may also be used. Further, as the light detector 207, an avalanche photodiode, a photomultiplier tube, or the like is employed for example.

As described above, by scanning the fundus in the x-axial and y-axial directions, sampling the reflected light in the ADC 210, and performing a signal processing in the calculator 500, the front image of the fundus of the subjected eye E can thereby be obtained.

Here, as the reflected light may be avoided at the mirror 204 by the polarization beam splitter, avoidance of the reflected light is an important task in the SLO optical system as well. Especially, the objective lens 109 is preferably provided with the reflectance reduction such as the antireflection coating or the like according to both of the wavelengths of the OCT measurement light and the SOL measurement light.

Third Embodiment

In this embodiment, measurement of an anterior eye using a multimode wavelength sweeping light source will be described. An OCT according to a third embodiment of the present disclosure will be described, however, only points different from the first embodiment will be described and an explanation of common points will be omitted.

Figure 5A:
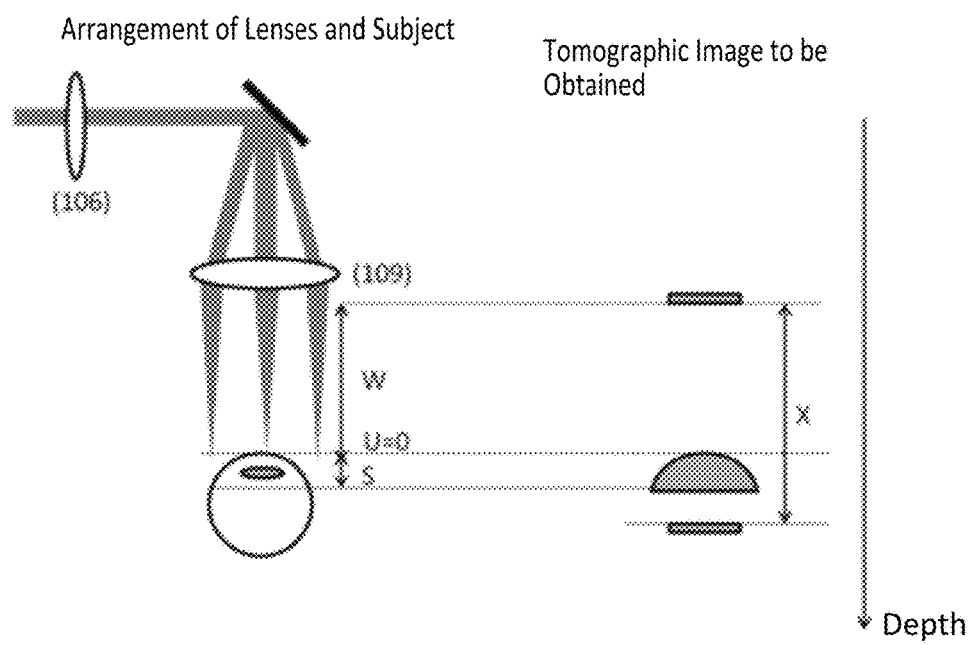
FIG. 5A is a diagram schematically showing B-scan tomographic images measured when a light path adjustment is performed in an optical coherence tomography of a third embodiment, virtually including an area outside of a depiction range.

FIG. 5A is a diagram explaining an optical system of an optical coherence tomography 2 of the present embodiment in detail. It should be noted that in the present embodiment, the subject is a human eye (eyeball) and a tomographic image to be obtained includes an anterior eye including a cornea, an anterior chamber, an iris, and a crystalline lens. A method according to this disclosure is not limited thereto, and may more limitedly measure only a vicinity of an anterior chamber angle or only the crystalline lens. Further, this optical system can be similarly applied to another part of a living matter, for example, a skin surface.

Other than light of which wavelength is similar to that of the retina OCT measurement light, light of which wavelength is 1250 to 1370 nm can be used as the OCT measurement light.

Here, in this embodiment, the predetermined operation distance W=71 mm, the depth U=0 mm due to the area of interest of the subjected eye being the anterior eye, and the range of the area of interest S=16 mm are adopted. All of these are optical distances. It is considered that this range of the area of interest S can cover differences among depth regions of individual anterior eyes.

Figure 6:
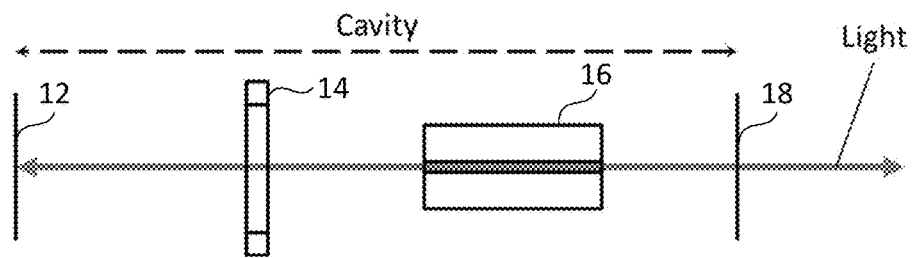
FIG. 6 shows a configuration of a wavelength sweeping light source comprising a straight cavity in the optical coherence tomography of the third embodiment.
Figure 7:
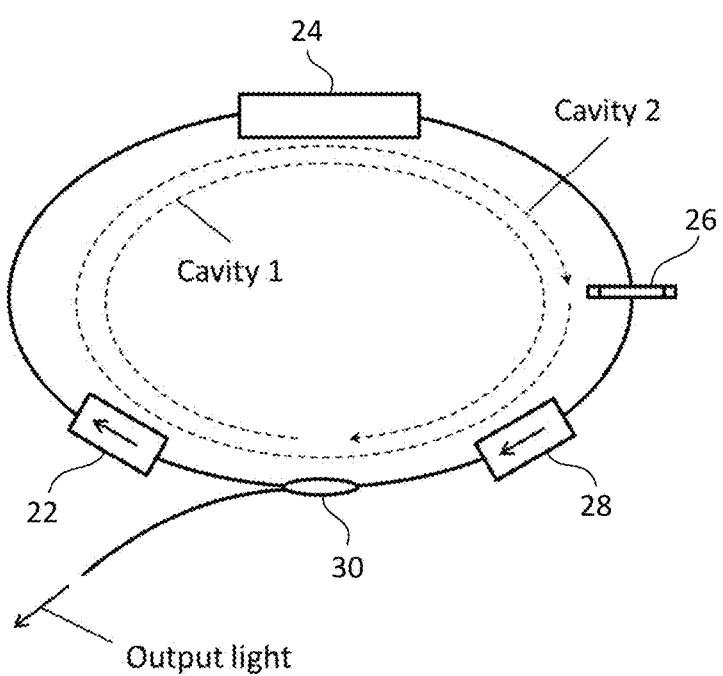
FIG. 7 shows a configuration of a wavelength sweeping light source comprising a fiber ring cavity in the optical coherence tomography of the third embodiment.

In the multimode wavelength sweeping light source, a cavity for oscillation corresponds to a pair of surfaces of at least one optical element, and reflected light according to a distance between the pair of surfaces of the at least one optical element is amplified by oscillation and affects interference light. For example, as shown in FIG. 6, a wavelength sweeping light source provided with a straight cavity comprises a mirror 12, a tunable Fabry-Perot filter 14, a gain medium 16, and a half mirror 18. In the wavelength sweeping light source provided with the straight cavity, surfaces of the mirror 12 and the half mirror 18 each of which intersects substantially perpendicularly with the optical axis constitute the pair of surfaces of the at least one optical elements. Further, as shown in FIG. 7, a wavelength sweeping light source provided with a fiber ring cavity comprises a plurality of isolators 22 and 28, a gain medium 24, a tunable Fabry-Perot filter 26, and a fiber coupler 30. In the wavelength sweeping light source provided with the fiber ring cavity, for example, both surfaces of the fiber coupler 30 constitutes the pair of surfaces of the at least one optical elements as in a cavity 1, and/or surfaces of two mirrors provided in the tunable Fabry-Perot filter 26 constitute the pair of surfaces of the at least one optical elements as in a cavity 2. Further, if reflection surfaces are provided in the isolators 22 and 28, and the gain medium 24, the reflection surfaces can constitute the pair of surfaces of the at least one optical elements. Accordingly, surfaces of optical element(s) intersecting substantially perpendicularly with the optical axis can constitute the pair of surfaces of the at least one optical surfaces. Therefore, the pair of surfaces of the at least one optical elements can be present not only in the cavity of the multimode wavelength sweeping light source, but also in the measurement light path and the reference light path. For example, surfaces of the collimator lens 103 and the focus lens 104 arranged in the measurement light path can constitute the pair of surfaces of the at least one optical elements. Further, in the reference light path as well, the collimator lens 110 and the prism 112, the collimator lens 110 and the collimator lens 111, and the collimator lens 111 and the prism 112 can each constitute the pair of surfaces of the at least one optical elements. As a result of preliminary measurement, interference light was observed in a frequency of X=90 mm. It should be noted that, although the pair of surfaces of the at least one optical elements is present not only in the multimode wavelength sweeping light source but also in the measurement light path and/or the reference light path, a distance between the pair of surfaces of the at least one optical elements in the measurement light path and/or the reference light path was greater than W+U+S=86 mm but not equal to or smaller than 90 mm.

The tomographic image generated on the above condition is schematically shown as in FIG. 5A. The reflection signal of the subject-side surface of the objective lens 109 appears at a position shallower by the operation distance W from the surface of the subject. Further, although the surface of the subject is not the artifact since it is the area of interest in this case, the multiple reflection between the surface of the subject and the objective lens 109 should be considered. However, since the light oscillated by the multiple reflections generated in the multimode wavelength sweeping light source has traveled a distance 2X, the reflection signal of the objective lens 109 appears at a position deeper by a distance X. In this case, this reflection appears at a position close to the subject, and thus this reflection needs to be dealt with importance.

If the pair of surfaces of the at least one optical elements which have the distance X therebetween is present in the measurement light path or the reference light path, such artifact occurs due to the multiple reflection signal being generated in a similar manner. For example, even when the multimode wavelength sweeping light source is not used, if the objective lens 109 and the lens 106 in FIG. 5A have the distance X therebetween, a similar problem occurs.

FIG. 5B shows tomographic images relative to various values of the position Z that the operator can obtain as the depiction range, including a situation outside of the depiction range virtually. Since the operation distance W is constant and the depth U=0 in the present embodiment, there is a complete correspondence relationship between the light path length adjustment range and changes in Z values.

In FIG. 5B, the light path length adjustment is performed with Z=0, and the area of interest moves to a deep position in the depiction range as the position Z becomes deep. In conjunction with that, the mirrored images of the reflection signals of the surface of the subject and the objective lens move to shallow positions. In this case, until the position Z becomes (W+U−S)/2=27.5 mm, the reflection signal of the objective lens does not reach the area of interest, and thus a depth position of the position Z can be freely determined within the range of Z=0 to 27.5 mm. On the other hand, when the position Z becomes shallow by the light path length adjustment, the mirrored image of the area of interest moves to a deep position, and the reflection signal does not reach this area of interest regardless of a value of the depth U, until the position Z becomes −(X−W−U)/2=−9.5 mm.

As described above, the range where the artifacts do not overlap the tomographic image is the range of Z=−9.5 to 27.5 mm. However, as described in the first embodiment, since the tomographic image of the area of interest looks replicated in the range of Z=0 to −16 mm substantially, the depth position can be freely determined in the range of Z=0 to 27.5 mm.

On the other hand, when the position Z becomes further shallower by the light path length adjustment, the range where the artifacts do not overlap the tomographic image is obtained at Z=−(X−W−U+S)/2=−17.5 mm. In a range where the position Z is shallower than that, it is possible to avoid at least the reflection signal of the objective lens and the reflection signal of the objective lens displaced by the distance X resulted from the cavity in the multimode wavelength sweeping light source.

Although the tomographic image is shown as the mirrored image at Z=−17.5 mm, since S=16 mm is adopted, the area of interest can be obtained without any artifacts overlapping by using a condition which is compatible with the depiction range to measure the tomographic image in a vicinity of the zero distance.

Considering the above on a general condition, the range shown in FIG. 5B corresponds to the following conditional formulas.

$$-(W-S)<U-2Z<X-W; \quad [a2]$$

$$U-2Z>X-W+S, \quad [c2]$$

Further, considering a broader range of the position Z than the range shown in FIG. 5B, a conditional formula corresponding to Z>(W+U)/2, namely [b1] U−2Z<−W is applied as well other than the above conditional formulas. If the value of the position Z satisfies at least one of these conditional formulas, it is possible to make any artifacts not overlap the tomographic image.

As above, in both cases where the value of Z is positive and where the value of Z is negative, the condition that does not make the artifacts overlap can be set. Since the depth is U=0 in the anterior eye, the light path length adjustment does not seem necessary if it was merely for image depiction. However, especially in the present embodiment, sensitivity for the tomographic image needs to be examined considering the use of the multimode wavelength sweeping light source.

With the multimode wavelength sweeping light source, there is a possibility that the coherence length is not sufficient relative to the depiction range. The coherence length needs to be 32 mm or greater to depict an entirety of the range S=16 mm, however, the length is relatively large for the multimode wavelength sweeping light source. In this case, signal sensitivity reduces at the deep position far from the zero distance. Therefore, it is more preferable that the setting can be switched especially between a case where the sensitivity for a shallow portion within the area of interest is thought important and a case where the sensitivity for a deep portion within the area of interest is thought important.

For example, in a case where a shape of the cornea of the anterior eye is analyzed, it is preferable that the sensitivity for the corneal surface is high, and the range of the position Z is Z>0 mm. On the other hand, in a case where the crystalline lens located at the deep position is observed as the subject with importance, it is preferable that the range of the position Z is Z<−17.5 mm such that the deep position becomes closer to the zero distance. Since an appropriate position varies depending on the subjected eye in the latter case, the continuous adjustment is needed at a minimum degree, however, it is more preferable that the light path length adjustment is set so as to be partially switched discretely.

In order to obtain such a light path length adjustment method, an optical configuration where two kinds of optical systems are provided in the measurement light path or the reference light path and the two optical systems can be switched from each other may be provided, such as a configuration disclosed in Japanese Patent Application Publication No. 2011-527418. Alternatively, software may control the measurement light path or the reference light path to be limited within certain range so that the operator would not be distracted by the control even if the light path length is continuously adjusted.

Notably, in the third embodiment, the depth U=0 mm is adopted, that is, the case has been assumed where the surface of the subject does not become the artifact explicitly. However, for example, if the depth U has a finite value and the surface of the subject is regarded as the artifact, the condition is slightly different. According to such an embodiment, for example, a case where only the crystalline lens is regarded as the area of interest is assumed.

In this case, as described in the first embodiment and FIG. 3C, a scheme considering the reflection of the surface of the subject can be applied. In the first embodiment, the condition is that the reflection being the artifact in the rearward to the subject is apart by the operation distance W from the surface of the subject. Considering the condition of the third embodiment, the position of the artifact is apart by X−W rearward. Therefore, the conditional formulas of the first embodiment can be formally replaced with the following conditional formulas related to the rearward artifact.

$$S<U-2Z<X-W \quad [a3]$$

$$U-2Z<-W \quad [b1]$$

$$U-2Z>X-W+S \quad [c2]$$

$$-(W-S)<U-2Z<0 \quad [d1]$$

Some of features of the optical coherence tomography disclosed herein will be listed hereinbelow.

Item 1. An optical coherence tomography comprising:
a light source configured to change a wavelength of light to be outputted;
a light separator configured to separate outputted light outputted from the light source into measurement light irradiated to a subject and reference light;
a light generator configured to generate interference light by multiplexing reflected light from the subject and the reference light;
a detector configured to detect the interference light;
a processor;
a memory storing computer-readable instructions therein, the computer-readable instructions, when executed by the processor, causing the optical coherence tomography to perform:

forming a tomographic image of the subject based on a result by the detector; and
a first optical element arranged on a measurement light path so as to be closest to the subject and intersect substantially perpendicularly with an optical axis of the measurement light path, the measurement light path being a light path of the measurement light and the reflected light from the subject, the first optical element satisfying at least one of following conditional formulas:

$$S<U-2Z<W; \quad [a1]$$

$$U-2Z<-W; \text{ and} \quad [b1]$$

$$U-2Z>W+S, \quad [c1]$$

$$-(W-S)<U-2Z<0 \quad [d1]$$

W: a predetermined operation distance being a distance between a subject-side surface of the first optical element and a surface of the subject
U: a depth of interest being a depth from the surface of the subject to an area of interest of the subject
S: a range of interest being a depth range of the area of interest
Z: a shallowest position of the area of interest relative to an origin position where a difference between a length of the measurement light path and a length of the reference light path becomes zero.

Item 2. An optical coherence tomography comprising:
a light source configured to change a wavelength of light to be outputted;
a light separator configured to separate outputted light outputted from the light source into measurement light irradiated to a subject and reference light;
a light generator configured to generate interference light by multiplexing reflected light from the subject and the reference light;
a detector configured to detect the interference light;
a processor;
a memory storing computer-readable instructions therein, the computer-readable instructions, when executed by the processor, causing the optical coherence tomography to perform:

forming a tomographic image of the subject based on a result by the detector;
a first optical element arranged on a measurement light path so as to be closest to the subject and intersect substantially perpendicularly with an optical axis of the measurement light path, the measurement light path being a light path of the measurement light and the reflected light from the subject,
at least one of second optical elements, comprising a pair of surfaces, the pair of surfaces of the at least one of the second optical elements being present in at least one of the light source, the measurement light path, and a reference light path being a light path of the reference light, the pair of surfaces of the at least one of the second optical elements intersecting substantially perpendicularly with an optical axis of the outputted light, the measurement light, or the reference light, wherein the first optical element satisfies at least one of following conditional formulas:

$$-(W-S)<U-2Z<X-W; \quad [a2]$$

$$U-2Z<-W; \text{ and} \quad [b1]$$

$$U-2Z>X-W+S, \quad [c2]$$

W: a predetermined operation distance being a distance between a subject-side surface of the first optical element and a surface of the subject U: a depth of interest being a depth from the surface of the subject to an area of interest of the subject S: a range of interest being a depth range of the area of interest X: a distance which is greater than W+U+S and minimal among distance(s) between the pair of surfaces of at least one of second optical elements Z: a shallowest position of the area of interest relative to an origin position where a difference between a length of the measurement light path and a length of the reference light path becomes zero.

Item 3. The optical coherence tomography of item 2, wherein the first optical element further satisfies at least one of following conditional formulas in a case where the first optical element satisfies the conditional formula [a2]:

$$S<U-2Z<X-W \quad [a3]$$

$$-(W-S)<U-2Z<0 \quad [d1]$$

Item 4. The optical coherence tomography of any one of items 1 to 3, further comprising a controller configured to change one of the measurement light path length and the reference light path length within a predetermined adjustment range, and at least one of the conditional formulas is satisfied within the adjustment range.

Item 5. The optical coherence tomography of item 4, wherein at least a part of the adjustment range is adjusted continuously.

Item 6. The optical coherence tomography of any one of items 1 to 5, wherein a coherence length of the light source is equal to or greater than U+S.

Item 7. The optical coherence tomography of any one of items 1 to 6, wherein a coherence length of the light source is equal to or greater than W-U+S.

Item 8. The optical coherence tomography of any one of items 1 to 7, wherein the light source is a multimode light source.

Item 9. The optical coherence tomography of any one of items 1 to 8, wherein the operation distance W is greater than U+S and equal to or less than 75 mm.

Item 10. The optical coherence tomography of any one of items 1 to 9, wherein the computer-readable instructions, when executed by the processor, cause the optical coherence tomography to further perform:

detecting the operation distance W.

Item 11. The optical coherence tomography of item 10, wherein the computer-readable instructions, when executed by the processor, cause the optical coherence tomography to further perform:

adjusting the operation distance W so as to be within a predetermined range based on a result of the detecting of the operation distance W.

Item 12. The optical coherence tomography of any one of items 1 to 11, wherein the measurement light travels on its light path for a segment, and then is split.

Item 13. The optical coherence tomography of any one of items 1 to 12, wherein a reflectance reduction treatment is given to the surfaces of the first optical element.

Item 14. The optical coherence tomography of item 13, wherein the reflectance reduction treatment achieves a reflectance of 1% or less relative to an input of the measurement light and/or the reference light to the surfaces of the first optical element.

Item 15. The optical coherence tomography of item 13 or 14, wherein at least one of a wavelength of the measurement light and a wavelength of the reference light, and a wavelength targeted by the reflectance reduction treatment are set in a range of 810 to 870 nm.

Item 16. The optical coherence tomography of item 13 or 14, wherein at least one of a wavelength of the measurement light and a wavelength of the reference light, and a wavelength targeted by the reflectance reduction treatment are set in a range of 980 to 1100 nm.

Item 17. The optical coherence tomography of item 13 or 14, wherein at least one of a wavelength of the measurement light and a wavelength of the reference light, and a wavelength targeted by the reflectance reduction treatment are set in a range of 1250 to 1370 nm.

Item 18. The optical coherence tomography of any one of items 1 to 17, wherein the computer-readable instructions, when executed by the processor, cause the optical coherence tomography to further perform:

obtaining a planar image of the subject.

Item 19. The optical coherence tomography of item 18, wherein the obtaining of the planar image of the subject includes irradiating light of which wavelength is different from that of the measurement light to the subject, and the light is planar image measurement light.

Item 20. The optical coherence tomography of item 13, wherein the computer-readable instructions, when executed by the processor, cause the optical coherence tomography to further perform:

obtaining a planar image of the subject by irradiating light of which wavelength is different from that of the measurement light to the subject, the light being planar image measurement light, and the reflectance reduction treatment achieves a reflectance of 1% or less relative to an input of the plane image measurement light to the surfaces of the first optical element.

Item 21. The optical coherence tomography of item 20, wherein a wavelength of the plane image measurement light and a wavelength targeted by the reflectance reduction treatment are set equal to or greater than 750 nm.

Item 22. The optical coherence tomography of any one of items 1 to 21, wherein the forming of the tomographic image of the subject includes performing a dispersion compensation of the subject by signal processing.

Item 23. The optical coherence tomography of any one of items 1 to 22, wherein the subject is an eye.

What is claimed is:

1. An optical coherence tomography comprising:
    a light source configured to change a wavelength of light to be outputted;
    a light separator configured to separate outputted light outputted from the light source into measurement light irradiated to a subject and reference light;
    a light generator configured to generate interference light by multiplexing reflected light from the subject and the reference light;
    a detector configured to detect the interference light;
    a processor;
    a memory storing computer-readable instructions therein, the computer-readable instructions, when executed by the processor, causing the optical coherence tomography to perform:
        forming a tomographic image of the subject based on a result by the detector;
    a first optical element arranged on a measurement light path so as to be closest to the subject and intersect substantially perpendicularly with an optical axis of the measurement light path, the measurement light path being a light path of the measurement light and the reflected light from the subject; and at least one of second optical elements comprising a pair of surfaces, the pair of surfaces of the at least one of the second optical elements being present in at least one of the light source, the measurement light path, and a reference light path being a light path of the reference light, the pair of surfaces of the at least one of the second optical elements intersecting substantially perpendicularly with an optical axis of the outputted light, the measurement light, or the reference light, wherein the first optical element satisfies at least one of following conditional formulas:

$$-(W-S)<U-2Z<X-W;$$ [a2]

$$U-2Z<-W;\text{ and}$$ [b1]

$$U-2Z>X-W+S,$$ [c2]

W: a predetermined operation distance being a distance between a subject-side surface of the first optical element and a surface of the subject U: a depth of interest being a depth from the surface of the subject to an area of interest of the subject S: a range of interest being a depth range of the area of interest X: a distance which is greater than W+U+S and minimal among distance(s) between the pair of surfaces of at least one of second optical elements Z: a shallowest position of the area of interest relative to an origin position where a difference between a length of the measurement light path and a length of the reference light path becomes zero.

2. The optical coherence tomography of claim 1, further comprising a controller configured to change one of the measurement light path length and the reference light path length within a predetermined adjustment range, and
at least one of the conditional formulas is satisfied within the adjustment range.

3. The optical coherence tomography of claim 1, wherein a coherence length of the light source is equal to or greater than U+S.

4. The optical coherence tomography of claim 1, wherein a coherence length of the light source is equal to or greater than W−U+S.

5. The optical coherence tomography of claim 1, wherein the light source is a multimode light source.

6. The optical coherence tomography of claim 1, wherein the operation distance W is greater than U+S and equal to or less than 75 mm.

7. The optical coherence tomography of claim 1, wherein the computer-readable instructions, when executed by the processor, cause the optical coherence tomography to further perform:
detecting the operation distance W.

8. The optical coherence tomography of claim 7, wherein the computer-readable instructions, when executed by the processor, cause the optical coherence tomography to further perform:

adjusting the operation distance W so as to be within a predetermined range based on a result of the detecting of the operation distance W.

9. The optical coherence tomography of claim 1, wherein the measurement light travels on its light path for a segment, and then is split.

10. The optical coherence tomography of claim 1, wherein a reflectance reduction treatment is given to the surfaces of the first optical element.

11. The optical coherence tomography of claim 10, wherein the reflectance reduction treatment achieves a reflectance of 1% or less relative to an input of the measurement light and/or the reference light to the surfaces of the first optical element.

12. The optical coherence tomography of claim 10, wherein at least one of a wavelength of the measurement light and a wavelength of the reference light, and a wavelength targeted by the reflectance reduction treatment are set in a range of 810 to 870 nm.

13. The optical coherence tomography of claim 10, wherein at least one of a wavelength of the measurement light and a wavelength of the reference light, and a wavelength targeted by the reflectance reduction treatment are set in a range of 980 to 1100 nm.

14. The optical coherence tomography of claim 10, wherein at least one of a wavelength of the measurement light and a wavelength of the reference light, and a wavelength targeted by the reflectance reduction treatment are set in a range of 1250 to 1370 nm.

15. The optical coherence tomography of claim 10, wherein the computer-readable instructions, when executed by the processor, cause the optical coherence tomography to further perform:
obtaining a planar image of the subject by irradiating light of which wavelength is different from that of the measurement light to the subject, the light being planar image measurement light, and
the reflectance reduction treatment achieves a reflectance of 1% or less relative to an input of the plane image measurement light to the surfaces of the first optical element.

16. The optical coherence tomography of claim 15, wherein a wavelength of the plane image measurement light and a wavelength targeted by the reflectance reduction treatment are set equal to or greater than 750 nm.

17. The optical coherence tomography of claim 1, wherein the computer-readable instructions, when executed by the processor, cause the optical coherence tomography to further perform:
obtaining a planar image of the subject.

18. The optical coherence tomography of claim 17, wherein
the obtaining of the planar image of the subject includes irradiating light of which wavelength is different from that of the measurement light to the subject, and
the light is planar image measurement light.

19. The optical coherence tomography of claim 1, wherein the forming of the tomographic image of the subject includes performing a dispersion compensation of the subject by signal processing.

* * * * *